Figure 2:
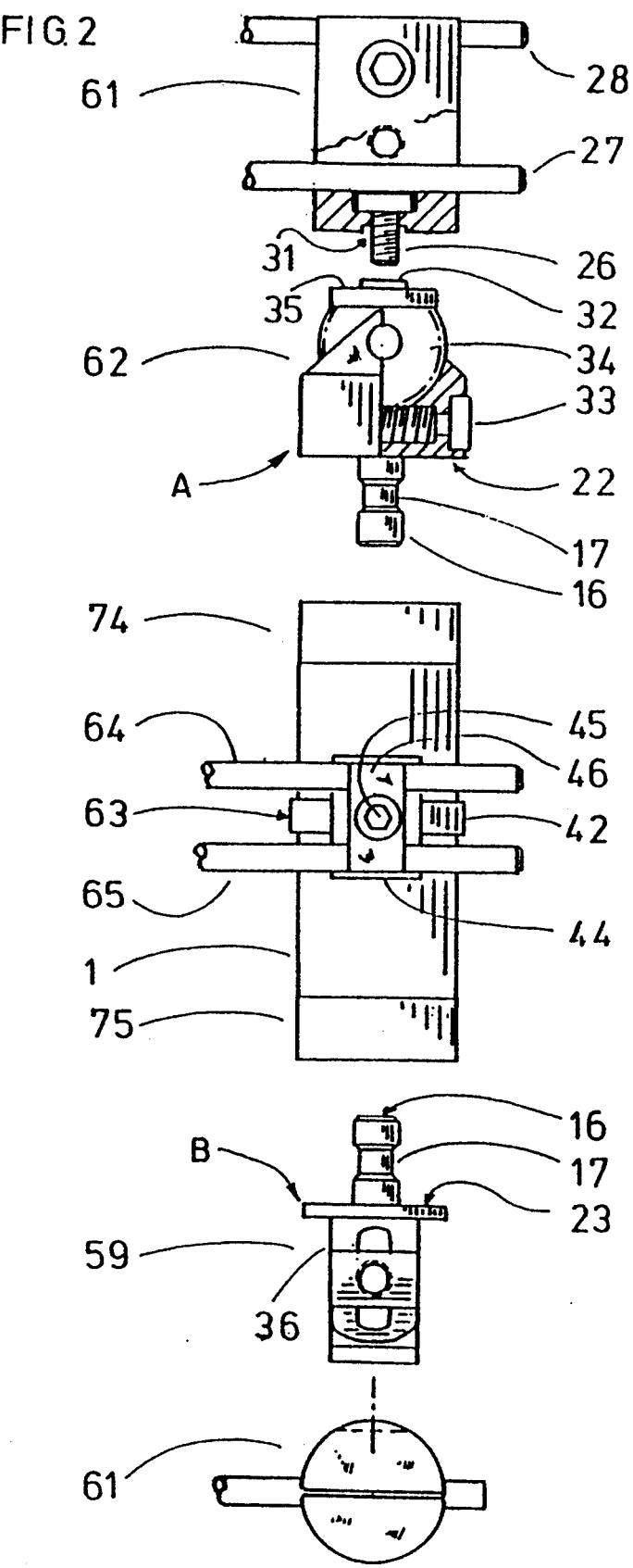

United States Patent [19]

Pfeil et al.

[11] Patent Number: 5,451,226
[45] Date of Patent: Sep. 19, 1995

[54] UNILATERAL, EXTENSIBLE, EXTERNAL TENSIONING DEVICE FOR TREATING BONE DISEASES

[76] Inventors: Joachim Pfeil, Robert-Bollschweilerstr. 5; Wolfgang Veith, Leisberg 7, both of D-6900 Heidelberg 1, Germany

[21] Appl. No.: 305,408

[22] Filed: Sep. 13, 1994

Related U.S. Application Data

[63] Continuation of Ser. No. 613,489, Dec. 11, 1991, abandoned.

[30] Foreign Application Priority Data

Mar. 6, 1989 [DE] Germany ............ 8902691 U
Jul. 26, 1989 [EP] European Pat. Off. ........... 89113809

[51] Int. Cl.⁶ .................................................. A61F 5/00
[52] U.S. Cl. .................................... 606/59; 606/57; 606/53
[58] Field of Search ............... 606/33, 54, 57, 72, 606/73, 53, 55, 56, 58, 59, 60

[56] References Cited

U.S. PATENT DOCUMENTS

| | | | |
|---|---|---|---|
| 2,346,346 | 4/1944 | Anderson | 128/92 |
| 4,096,857 | 6/1978 | Cramer et al. | 606/57 |
| 4,312,336 | 1/1982 | Danieletto et al. | 606/57 |
| 4,615,338 | 7/1986 | Ilizarov et al. | |
| 4,621,627 | 11/1986 | DeBastiani et al. | 606/57 |

FOREIGN PATENT DOCUMENTS

| | | | |
|---|---|---|---|
| 0024256 | 2/1981 | European Pat. Off. | |
| 0153546 | 4/1985 | European Pat. Off. | |
| 2557933 | 7/1985 | European Pat. Off. | |
| 851028 | 1/1940 | France | |
| 1206411 | 2/1960 | France | |
| 2274266 | 1/1976 | France | |
| 2110094 | 6/1983 | United Kingdom | |
| 8602822 | 5/1986 | WIPO | 606/57 |

*Primary Examiner*—Sam Rimell
*Attorney, Agent, or Firm*—Baker & Daniels

[57] ABSTRACT

The invention concerns a unilateral, extensible external tensioning device for treating bone disease and for the purpose of axially and externally affixing bones or parts of fractured bones. At least one piston is mounted on both sides in telescoping manner to a central portion with various linking mechanisms being rotatably attachable to the outer ends of the pistons for receiving bone screw clamping mechanisms.

22 Claims, 8 Drawing Sheets

FIG.1
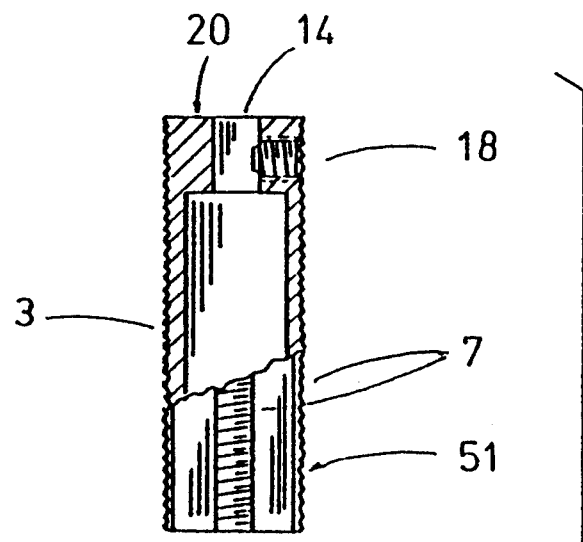
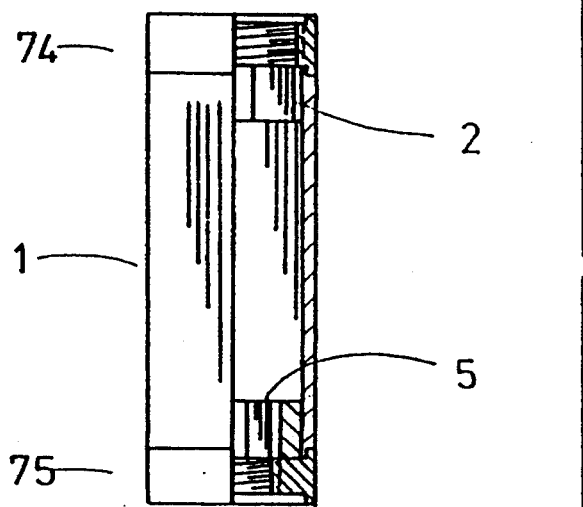
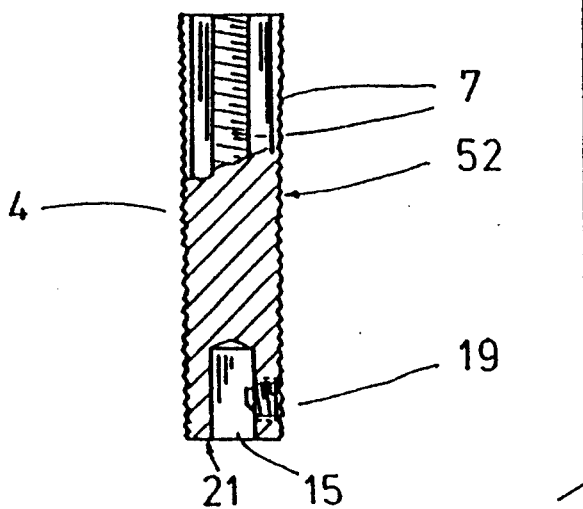

UNILATERAL, EXTENSIBLE, EXTERNAL TENSIONING DEVICE FOR TREATING BONE DISEASES

This is a continuation of application Ser. No. 07/613,489, filed Dec. 11, 1991 abandoned.

The invention concerns a unilateral, extensible, external tensioning device for treating bone diseases.

Such an orthopedic device is described in the U.S. Pat. No. 4,312,336 for the axial, external fixation of bones or bone fragments.

Already unilateral screw affixing device for treating bone diseases of the extremities have been described several times. The multitude of different bone diseases sets different requirements on external fixation. Accordingly a kit system meeting the diverse requirements shall be advantageous. The apparatus described herein meets many demands in external fixation. It also makes possible taking care of double stage fractures, mono- and bi-focal extension, also motor-driven extension and callus stimulation. As regards pseudo-arthrosis, it allows fragment displacement. Also the described apparatus permits continuous change in all directions of motion.

Comparable orthopedic devices, for instance as described in the German patent 3,543,402 (Orthofix), are only able to take care of part of the above indications and especially it has been impossible heretofore to take care of double-stage fractures, bifocal extensions and continuous changes or motor-driven extensions and fragment shifting using the Monofixateur (single affixing means). As regards these indications, affixing means heretofore were required, which are difficult to put in place by operation and which perforate the skin from several directions. The previously available orthopedic devices suffered from the drawback that depending on the location of the indication, a completely new device had to be used, because illustratively it was impossible by means of one device to carry out both fracture care and extension. The previous systems moreover incurred the drawback that different parts had to be mounted on the affixing means during treatment, and as a consequence frequently parts of this affixing means were lost and unnecessary additional costs were borne.

Accordingly it is the object of the present invention to create a unilaterally extensible external tensioning device for treating bone diseases, the pertinent bone segments being fixed in position relative to each other, tensioned, shifted in controlled manner and be dynamized in guided, dynamic, irrotational manner by means of bone screws held in clamping jaws.

This problem is solved by the invention in that at least one piston is mounted in extensible manner on each side of a tubular central part, various link means being attachable in rotatable manner to the outer ends of the inner pistons.

The scope of the invention is such as to provide both two pistons only in the central part on one hand, and two further telescoping pistons inside the above pistons on the other. The links are always mounted to the innermost piston.

The orthopedic device of the invention makes it possible on account of the special double telescoping and the high strength of the articulating links relative to flexure to use only one type of affixing device for the lower extremity and a further type of affixing device for the upper one. This means that fewer types of bone-fixation devices need be stored in an orthopedic or emergency clinic, while on the other hand the scope of indications of this device is much wide than for comparable single fixation means. The orthopedic device of the invention is designed in such a way that before treatment and with corresponding problem definition, various parts are apposed in the manner of the kit system. Therefore no part shall be removed during treatment, and there is no danger of losing any.

The advantages made possible in this manner can be summarized as follows:

By means of one size each for the lower and upper extremities, the orthopedic device described herein makes it possible to treat all bone diseases wherein the indication points to a fixation device. No parts are screwed on or off the orthopedic device during treatment and therefore there is no danger of losing any during it. Handling is technically comprehensible and simple. Nevertheless a large scope of indications is covered by the orthopedic device.

Especially preferred embodiments of the unilateral, extensible, external tensioning device of the invention are described in the claims.

A specific length of the central part and the two pistons can be set by means of the telescoping pistons. Various links may be fastened by a clamping pin to the pistons, and bone screw clamping jaws in turn may be affixed to said pin. Especially preferred designs are provided for the links, for instance an articulating joint plugged by means of the clamping pin onto the piston end and allowing spatial adjustment and fixation of a screwed-on bone screw clamping jaw.

These bone screw clamping jaws can be screwed-on longitudinally and/or transversely (so-called T jaws).

Again a rigid intermediate part is preferentially provided as a link which also can be plugged by a clamping pin onto the piston end, comprising an inside thread opposite the said piston end to screw-on a bone screw clamping jaw.

Also, a so-called switch is provided as a link, which implements by means of a self-locking worm drive the defined pivoting motion of the platform mounted to said worm.

Further it is possible to use a hinge means to be clamped at an arbitrary site as a link and which upon release of the clamping serves to dynamize joints in the plane of the hinge rotation.

A periodic in-and-out motion of the piston through the intermediary of the Schanz screws causes growing micro-motion of the fracture site and thereby callus stimulation; a variety of embodiments are feasible in this respect. Illustratively a flange-mounted step motor may be driven in such a way that the adjustment nut shall be rotated counterclockwise at the desired rate. The piston in such a case also would move in and out and the fracture site thereby would experience a growing micro-motion.

As described, the rotating adjustment nuts control the piston-setting relative to the central part. In principle it is possible to provide an adjustment nut detachable from the central part and remaining on the piston in order achieve quick setting to match the anatomical particulars or for purposes of dynamization.

In principle, an adjustment nut detachable from the central part can be provided, which remains on the piston to allow rapid adjustment to match anatomical particulars or to allow dynamization.

Next the invention shall be elucidated in relation to the attached drawings.

Figure 3:
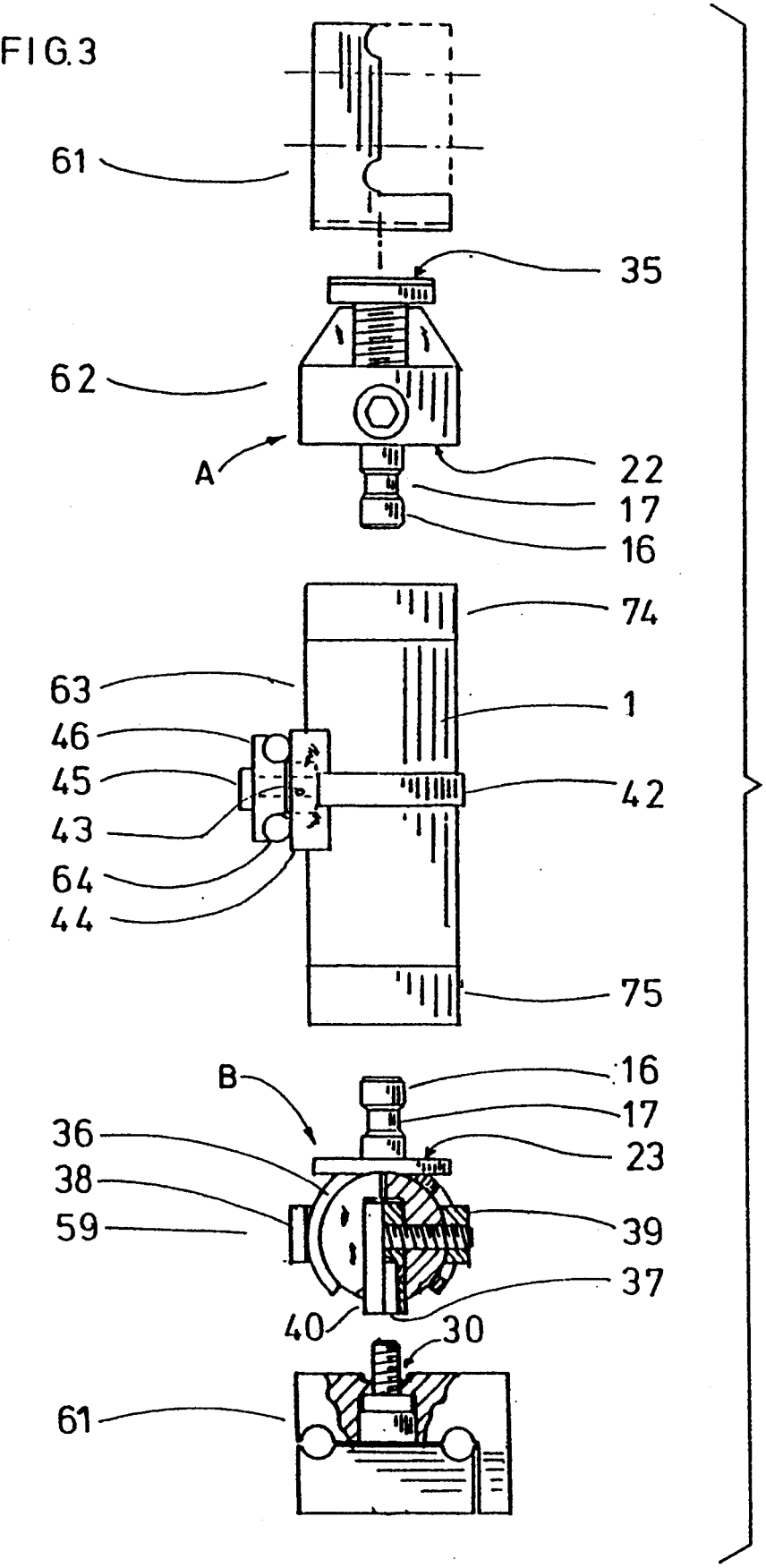
Figure 4:
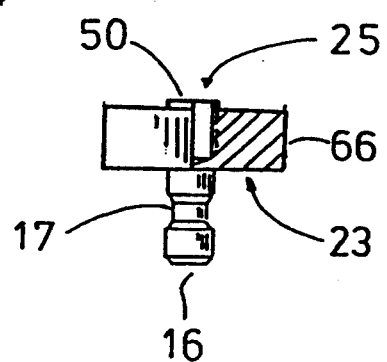
Figure 5:
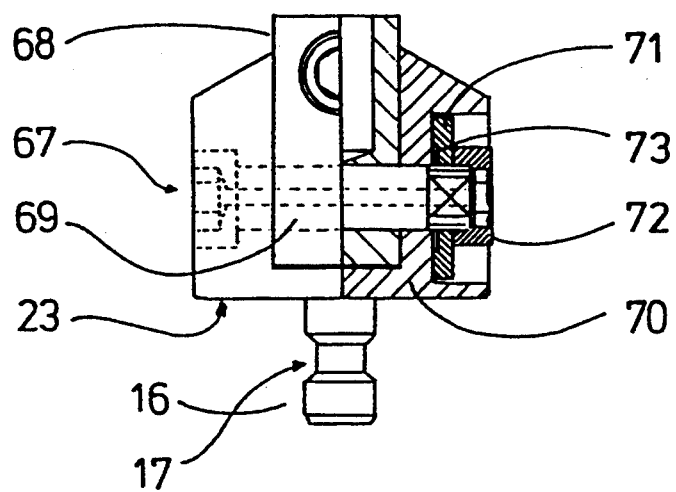
Figure 6:
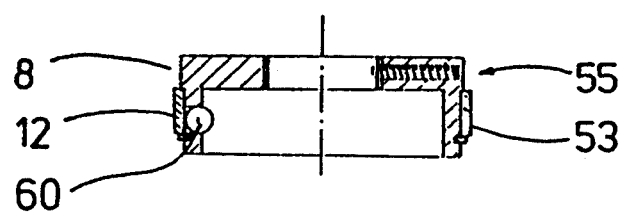
Figure 7:
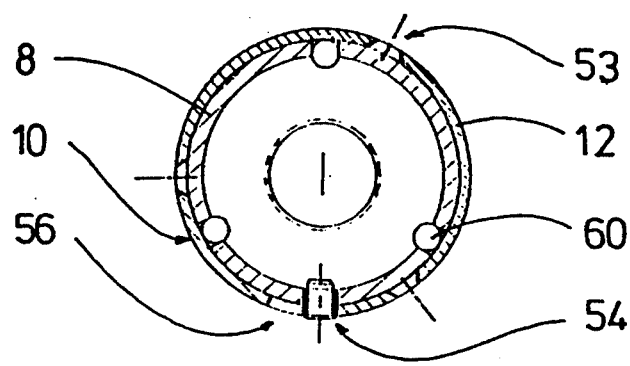
Figure 8:
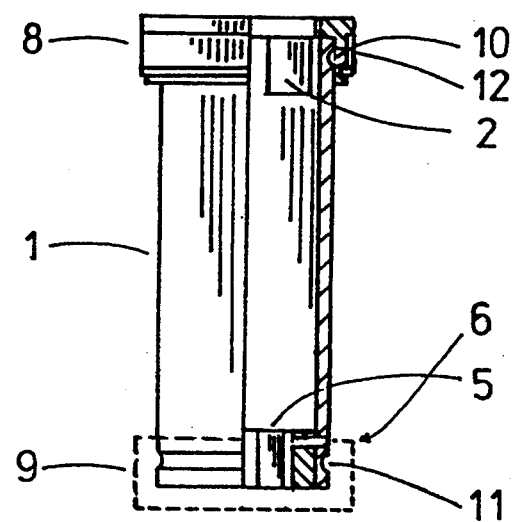
Figure 9:
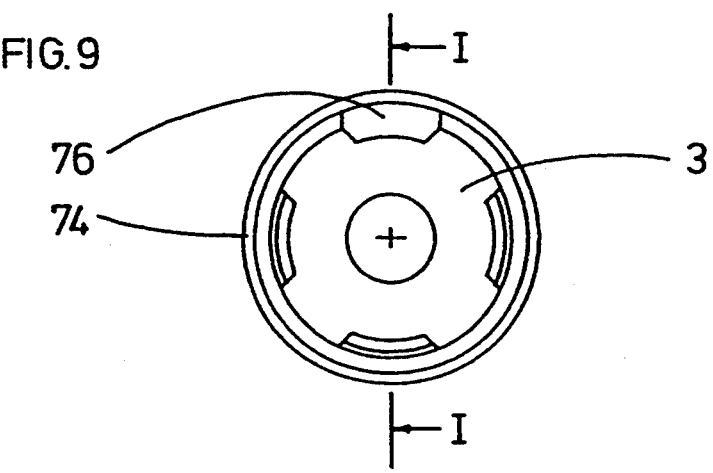
Figure 10:
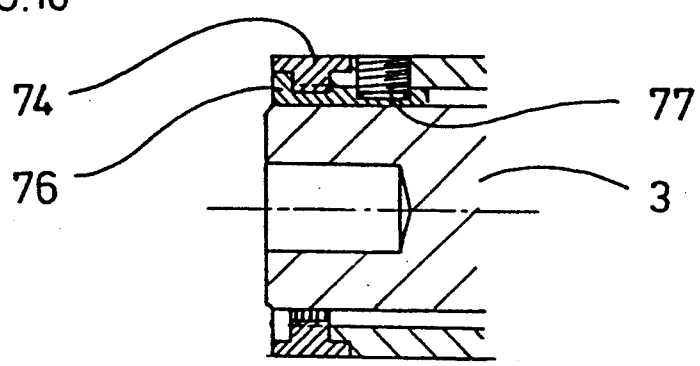

FIG. 1 shows the central part and the two pistons of the external tensioning device in partly sectioned form, FIG. 2 is the elevation of the various parts of the external tensioning device in partly sectioned form, FIG. 3 is a sideview in partial sectioned form of the parts of FIG. 2, FIG. 4 is a rigid intermediate part, FIG. 5 is a clamping hinge, FIG. 6 is the section of the adjustment nut 8 and the ring 12 of FIG. 8, FIG. 7 is the cross-section of the adjustment nut 8 and the ring 12 shown in FIG. 6, FIG. 8 is the partially sectioned elevation of a further central part, FIG. 9 is the topview of the central part shown in FIG. 1, with retracted piston 3, and FIG. 10 is the section I—I of FIG. 9.

Essentially FIG. 1 shows the central part 1 and the pistons 3 and 4 of the external tensioning device. The tubular central part 1 comprises a spline socket 2 wherein is guided the hollow piston 3 which for that purpose is provided with a matching spline or key toothing 7 over its entire length. The central part 1 and the extensible piston 3 thereby are secured against rotation on one hand while on the other hand free axial motion of the two parts is ensured. This is especially significant in dynamization. In order to clarify and discuss the individual parts, they are shown in exploded view in FIG. 1, but it is clear from the description that both the piston 3 the piston 4 act in concert with the central part 1.

The solid piston 4 opposite piston 3 also is provided over its entire length with the spline or key serration 7. It is guided by a correspondingly inside-serrated bush 5 fitted into the tubular end of the central part 1.

Both pistons 3 and 4 may be telescoped into the central part 1, i.e. into each other (4 into 3). The maximum length possible is achieved by extending both pistons 3 and 4, the central part 1 being extended almost by a factor of three. The required overlap of the spline at both ends of the central part reduces that length, being necessary to secure axial guidance and force transmission.

To allow a specific extension or shortening of the external tensioning device even when it is subjected to forces, both pistons 3, 4 comprise threads 51, 52 resp. which preferably shall be of the same pitch. The adjustment nut 74, 75 fitted with the matching inside thread allows axially displacing the piston 3, 4 relative to the central part 1. The displaceability of the two pistons 3, 4 is independent of that of the other.

The two adjustment nuts 74 and 75 are identical except for the different inside threads corresponding to the different piston cross-sections. The operation of these adjustment nuts 74, 75 is illustrated in FIGS. 9, 10. They are guided by means of one or more slide blocks.

The adjustment nuts 74, 75 are linked in rotatable manner to the central part 1. By rotating the adjustment nut 74, 75, the respective piston 3,4 shall retract or advance.

FIG. 2 shows the various parts of the external tightening device, partly in section, in the dismantled state.

FIG. 3 shows the parts of FIG. 2 in sideview. FIGS. 2 and 3 are discussed below. FIGS. 4 and 5 show further possible links for the external tensioning device.

As shown by FIG. 1, the boreholes 14, 15 are located respectively at the outer end of the piston 3,4 and the link means or linking mechanisms A and B shown in FIGS. 2, 3, 4 and 5 may be installed in said borehole using a pin 16.

The pin 16 comprises an annular recess 17 with bevelled sides, and this recess can be entered by correspondingly bevelled set screws 18, 19 resp. (FIG. 1). The moment the screw 18, 19 slightly enters the annular recess 17 of the pin 16 inserted into the borehole 14, 15, said pin no longer can slip away, while free rotation on the other hand is preserved. The end face of the piston 3,4 is provided with a radial knurling 20, 21. A corresponding knurling 22, 23 is present at the opposing side of the respective link means A and B. When the set screw 18, 19 is turned in all the way, the bevels on the screws and on the recess fully tighten the additional element (link) against the end face of the piston, the radial knurling or serration preventing mutual rotation of the two parts.

The uppermost part shown in FIGS. 2 and 3 is a bone screw clamping jaw 61 which can be affixed by an axial set screw 26 to the respective link means A. To prevent the jaw 61 from rotating relative the particular added part, a longitudinal groove 31 is present at the lower side in the area of the screw and is entered by a matching longitudinal key 32 (or 40, 50, 68) at the communicating side of the link means. The clamping jaw 61 is divided centrally and longitudinally above the screw head. It is fitted on both part surfaces with semi-round grooves transverse to the center axis of the jaw 61 and serving to receive the bone screws 27 and 28. These bone screws are tightened by screwing-on the upper part.

The lowermost portion of FIGS. 2 and 3 shows the described clamping jaw 61 having been rotated by 90° so that the linkage plane of the two bone screws is perpendicular to the central axis of the external tensioning device. In this case the screwing of the clamping jaw 61 to the particular link takes place by means of a hexagon socket screw. Again the clamping site is provided with a groove 30 to prevent rotation.

Below the clamping jaw 61 shown as the uppermost component in FIGS. 2 and 3, there is a switch 62 incorporating the link means A. The defined rotation of the platform 35 is achieved by said switch by means of a self-locking worm drive consisting of the worm shaft 33 and a worm gear 34. Illustratively the clamping jaw 61 may be screwed in rotation-secure manner on this platform 35. The worm is driven using a hexagonal socket at its end.

FIG. 2 shows a second component in its lower part in the form of an articulating link 59 incorporating the link means B which basically is a universal joint that, together with the rotatability of the clamping pin 16, allows pivoting the screw-tightened clamping jaws 61. A partly slotted circular segment 36 encloses the cylindrical inner part 37. The through-bolt 38 guided in the slot of the circular segment 36 passes through the inner part 37 which can rotate by a specified angle about its axis of rotation. Clamping of the inner part 37 takes place by means of a hexagonal socket screw but the nut 39 cannot rotate relative to its support because of its shape matching the convex outside of the circular segment 36 and a key entering the groove. As a result, the clamping screw 38 can be tightened using only one key and without having to hold another part in place.

A square bar 40 pivotable to both sides in a plane perpendicular to the cylinder axis is present in a slotted clearance of the inner element 37 and also may be clamped in place by the through-bolt 38. To improve security against rotation, a radial knurling is provided in the region of the bolt borehole 38 not only on both sides of the square bar but also on the insides of the cylindrical clearance 37 facing it. The square bar 40 comprises an inside thread so that by means of a screw the clamping jaw 61 may be tightened to it.

The central part of the external tensioning device shown by FIGS. 2 and 3 displays the bone-segment fixation device 63. A ring 42 matching the outside diameter of the central part 1 upon removal of the adjustment nut is mounted at an arbitrary location on the central part 1. A cylindrical element 43 with inside thread is present at the circumference. A platform 44 shaped in relation to the periphery of the central part 1 encloses the element 43 and comprises a clearance in the area of the ring 42 below it. If now pressure is exerted by the screw 45 through the upper clamping jaw 46 and the bone screws 64 and 65 in-between on the platform 44, then this platform shall be tightened at the desired location to the central part 1. In this case the clamping jaw 46 is rotatable through a specific angular range about the axis of the screw 45, making possible the alignment of the bone screws 64 and 65 holding the bone segment. To prevent undesired rotation, a radial serration is present at the lower side of the clamping jaw 46 and on its rest 43, which will mutually engage during clamping.

FIG. 4 shows another line 11 which may be used in lieu of the switch 62 or articulating link 59 of FIGS. 2 and 3. The rigid intermediate part 66 shown in FIG. 4 comprises the above described pin 16 acting as the clamping element. Opposite this pin 16 there are the inside thread 25 and the key 50 with which the described bone screw clamping jaw 61 can be screwed-on in irrotational manner. This intermediate part 66 also comprises the knurling 23.

FIG. 5 shows a clampable hinge joint 67. This hinge joint 67 can be clamped anywhere and upon clamping release serves to dynamize joints in the plane of the hinge motion.

The pivoting square bar 68 is rigidly joined to the pivot bolt 69 supported in an element 70 that, in U-shaped manner, encloses the square bar 68. The end of the pivot bolt 69 projecting beyond the element 70 is threaded and is milled flat on two mutually opposite sides. The disk 71 is radially serrated on one side and is mounted in irrotational manner, by means of a borehole matching the bolt cross-section, on the pivot bolt 69.

A spiral spring 73 wound between the element 70 and the disk 71 around the pivot bolt 69 keeps the disk 71 spaced from the element 70. Too, the element 70 is provided with a matching radial serration on the side facing this disk 71. If now the disk 71 is pressed by the nut 72 against the serration, the entire hinge 67 will be locked. A seat and a pin 16 are provided in the square bar 68 and the element 70 respectively for providing a pin connection like that described above in relation to FIGS. 2 and 3.

As regards the partly sectional elevation of the central part 1 shown in FIG. 8, the adjustment nut 8 or 9 always is located at the end of the central part. The operation of these nuts 8 and 9 now will be described in relation to FIGS. 6, 7 and 8.

The correspondingly internally serrated bush 5 fitted into the tubular end of the central part 1 serves to guide the solid piston—which is omitted from FIG. 8 but corresponds to the piston 4 shown in FIG. 1. This bush 5 is secured by a set screw 6 which, when being turned in the continuous inner thread borehole, can be made to project from the inside of the bush 5 and thereby can additionally clamp the solid piston 4.

The two adjustment nuts 8 and 9 comprise inside threads corresponding to the threads 51 and 52 respectively present on the raised outer parts of the pistons 3 and 4. These adjustment nuts 8 and 9 allow axially displacing the pistons 3 and 4 relative to the central part 1.

The two adjustment nuts 8 and 9 are identical except for the inside threads formed for the different piston cross-sections. The nuts 8 and 9 enclose like collars the particular ends of the central part 1. These collars comprise boreholes 10 on their peripheries to receive balls 60; the boreholes 10 taper inward and allow the balls 60 to partly project but prevent them from dropping out.

A semi-annular recess 11 at the level of the central plane of the balls 60 revolves along the circumference of both ends of the central part. The adjustment nut 8 or 9 accordingly is rotatably connected to the central part 1. The receding of the balls 60 prevents a ring 12, which is enclosed in freely rotatable manner by a split ring, and which encloses the collar (adjustment nut 8 or 9). When the adjustment nut 8 or 9 is rotated, mutually opposed axial forces act on the central part 1 and on the pertinent pistons 3 or 4, and the particular piston 3 or 4 appropriately advances or retracts.

For purposes of instrumentation or dynamization, it is desirable to loosen the axial connection provided by the adjustment nut 8 or 9 between the piston 3 or 4 resp. and the central part 1. For that purpose the ring 12 of FIGS. 6 and 7 is provided at its rim with a number of conically, outwardly tapering boreholes 53 matching the number of balls and their positions and which, while offset circumferentially equidistantly, shall be masked upon rotation of the ring 12 with the boreholes 10 in the collar part (adjustment nut 8 or 9), whereby the balls 60 may recede centrifugally without being able to drop out. FIGS. 6 and 7 show the adjustment nut 8. However the adjustment nut 9 is of similar design and cooperates with a corresponding ring 12.

A screw 54 located at the level of the central plane of the balls 60 in the collar on account of a corresponding clearance 56 in the circumference of the ring 12 allows restriction of the rotating path and stopping of the rotating ring 12. A radial set screw 55 present in the thread plane of the adjustment nut 8 or 9 allows affixing the nut 8 or 9 detached from the central part 1 at an arbitrary location of the piston 3 or 4. This permits limited dynamization of the bone segment supported by the external tensioning device. In relation to the selected axial segment, only deforming forces of defined magnitude shall be applied to the bone.

In lieu of the just above described adjustment nuts 8 and 9 of FIG. 8, the FIG. 1 shows the adjustment nuts 74 and 75 of which the operation shall now be described in relation to FIGS. 1, 9 and 10. FIG. 9 is the topview of the central part 1 with retracted piston 3, and shows the adjustment nut 74. The adjustment nut 75 operates similarly and shall not be described in detail hereafter.

In this embodiment mode, one or several slide blocks 76 may move in at least one or several key grooves 76 on the piston 3. On account of a recess in the form of an annular arc of circle in the vicinity of the thread of the adjustment nut 74, the slide block 76 is constrained to follow the axial motion of the adjustment nut 74 on the piston 3. The rim projecting on the central side of the slide block 76 also comprises a recess. This latter recess is entered by a radially mounted screw 77 of the central part 1, and thereby this screw hampers the slide block 76 regarding axial displacement.

Accordingly rotation of the adjustment nut 74 results in an appropriate extension or retraction of the pertinent piston 3. If the screw is 77 is tightened-in hard, then it shall press the slide block 76 firmly into the key's groove and thereby the piston 3 is prevented from moving axially, i.e. the adjustment nut 74 prevented from rotating. If the screw 77 in the central part 1 is turned out, then the pertinent piston 3 can be pulled out of the central part 1 in order to effect a quick adjustment.

We claim:

1. An extensible external fixation device for bones comprising:
   an elongate central body member having a longitudinal axis;
   at least one piston telescopically connected to said central member and axially displaceable relative thereto, said piston and said central member being non-rotatable relative to each other;
   adjustment means interconnecting said piston and said central member for creating mutually opposed forces acting directly along said longitudinal axis for selectively extending and retracting said piston and central member relative to each other;
   a clamping mechanism for holding at least one bone screw; and
   a linking mechanism disposed on said longitudinal axis rotatably interconnecting said clamping mechanism and an extending end of said piston for universal movement of said clamping mechanism relative to the extending end of said piston.

2. The fixation device as defined in claim 1, wherein two axially displaceable pistons are provided, each extending from a respective end of said central body member and including respective linking mechanisms and clamping mechanisms releaseably secured thereto.

3. The fixation device as defined in claim 2 further comprising fixing pins extending from said linking mechanisms, wherein each of said pistons includes a central bore hole in an outer end thereof for receiving a respective said fixing pin of a respective said linking mechanism.

4. The fixation device as defined in claim 2, wherein at least one of said pistons includes a central bore and the other of said pistons is received within said central bore of said one of said pistons.

5. The fixation device as defined in claim 4, wherein said one of said pistons is rotationally fixed and axially moveable within said central body member and said other of said pistons is rotationally fixed and axially moveable within said one of said pistons.

6. The fixation device as defined in claim 1, wherein said linking mechanism is rotationally fixed relative to the extending end of said piston.

7. The fixation device as defined in claim 1, wherein one of said central body member and said piston includes a plurality of mutually spaced axially extending grooves and the other of said central body member and said piston includes a corresponding number of splines received in said grooves for permitting axial displacement of said piston.

8. The fixation device of claim 1, wherein said adjustment means comprises a rotatable threaded member at one end of said central member and wherein said threaded member threadedly engages said piston.

9. The fixation device of claim 1, wherein:
   two axially displaceable pistons extending from opposite ends of said central member are provided, each of said pistons including respective linking mechanisms and clamping mechanisms secured thereto, and
   said adjustment means comprises a rotatable nut on each end of said central member in threaded engagement with respective said pistons.

10. The fixation device as defined in claim 9, wherein said linking mechanisms comprise ball and socket joints.

11. The fixation device as defined in claim 1, further comprising an intermediate clamping mechanism detachably mounted on said central body.

12. The fixation device as defined in claim 1, wherein said linking mechanism is an articulating link.

13. The fixation device as defined in claim 1, wherein said linking mechanism is a hinged joint pivotable about an axis substantially transverse to said longitudinal axis.

14. The fixation device as defined in claim 13, wherein said linking mechanism includes a worm gear and a follower such that rotation of said worm gear pivots said clamping mechanism about the axis substantially transverse to said longitudinal axis.

15. The fixation device of claim 1, wherein said linking mechanism includes a ball and socket joint.

16. An extensible external fixation device for bones comprising:
   an elongate central body member having a longitudinal axis;
   at least one piston telescopically connected to said central member and axially displaceable relative thereto, said piston and said central member being non-rotatable relative to each other;
   adjustment means disposed internally of one of said piston and said central member and interconnecting said piston and central member for creating mutually opposed forces for selectively axially extending and retracting said piston and central member relative to each other, said forces originating internally within one of said piston and said central member;
   a clamping mechanism for holding at least one bone screw; and
   a linking mechanism disposed on said longitudinal axis rotatably interconnecting said clamping mechanism and an extending end of said piston for universal movement of said clamping mechanism relative to the extending end of said piston.

17. The fixation device of claim 16, wherein said adjustment means comprises a rotatable threaded member at one end of said central member and wherein said threaded member threadedly engages said piston.

18. The fixation device of claim 16, wherein:
   two axially displaceable pistons extending from opposite ends of said central member are provided, each of said pistons including respective linking mechanisms and clamping mechanisms secured thereto, and
   said adjustment means comprises a rotatable nut on each end of said central member in threaded engagement with respective said pistons.

19. The fixation device of claim 16, wherein said linking mechanism includes a ball and socket joint.

20. An extensible external fixation device for bones comprising:
- an elongate central body member having an axial bore therein disposed along a longitudinal axis of said central member;
- at least one piston telescopically received in said bore and having threads thereon, said piston being axially displaceable relative to said central member, said piston and said central member being non-rotatable relative to each other;
- threads on said central member that are engaged with the threads on said piston whereby rotation of said central member threads selectively causes said piston to extend and retract relative to said central member;
- a clamping mechanism for holding at least one bone screw; and
- a linking mechanism disposed on said longitudinal axis rotatably interconnecting said clamping mechanism and an extending end of said piston for universal movement relative to the extending end of said piston.

21. The fixation device as defined in claim 20, including:
- a second piston telescopically received in said bore and having threads thereon, said second piston being axially displaceable relative to said central member and rotationally fixed against movement about said axis relative to said central member;
- second threads on said central member that are engaged with the threads on said second piston whereby rotation of said second threads selectively causes said second piston to extend and retract relative to said central member;
- a second clamping mechanism for holding at least one bone screw; and
- a second linking mechanism disposed on said longitudinal axis rotatably interconnecting said second clamping mechanism and an extending end of said second piston for universal movement relative to the extending end of said second piston.

22. The fixation device as defined in claim 21, wherein said threads on said central member that are engaged with the threads on said first mentioned and second piston, respectively, are carried on nuts that are rotatable relative to said central member.

* * * * *